US012673148B2

(12) United States Patent
Petralia et al.

(10) Patent No.: US 12,673,148 B2
(45) Date of Patent: Jul. 7, 2026

(54) EQUIPMENT FOR THE SUPPORT OF BIOMEDICAL DEVICES DURING EXTRACORPOREAL CIRCULATION AND RELATED SYSTEM

(71) Applicant: EUROSETS S.R.L., Medolla (IT)

(72) Inventors: Antonio Petralia, Medolla (IT); Nicola Ghelli, Medolla (IT); Paolo Fontanili, Medolla (IT); Marco Corbelli, Medolla (IT)

(73) Assignee: EUROSETS S.R.L., Medolla (IT)

( * ) Notice: Subject to any disclaimer, the term of this patent is extended or adjusted under 35 U.S.C. 154(b) by 326 days.

(21) Appl. No.: 18/563,905

(22) PCT Filed: May 27, 2022

(86) PCT No.: PCT/IB2022/055015
§ 371 (c)(1),
(2) Date: Nov. 23, 2023

(87) PCT Pub. No.: WO2022/254300
PCT Pub. Date: Dec. 8, 2022

(65) Prior Publication Data
US 2024/0226406 A1     Jul. 11, 2024

(30) Foreign Application Priority Data

May 31, 2021     (IT) ........................ 102021000014273

(51) Int. Cl.
*A61M 1/36*          (2006.01)
*A61M 60/113*        (2021.01)
(Continued)

(52) U.S. Cl.
CPC .......... *A61M 1/367* (2013.01); *A61M 1/3666* (2013.01); *A61M 60/113* (2021.01);
(Continued)

(58) Field of Classification Search
CPC ............ A61M 1/3666; A61M 2209/08; A61M 2209/084; A61M 60/232; A61M 60/113;
(Continued)

(56) References Cited

U.S. PATENT DOCUMENTS 4,627,618 A * 12/1986 Schwartz ............. A63B 21/072
                                              482/108
4,998,337 A *  3/1991 Tiekink ............. B29C 66/52291
                                              29/521
(Continued)

FOREIGN PATENT DOCUMENTS

CA        2 361 604 A1    8/2000
CN    110 404 129 A       11/2019
(Continued)

*Primary Examiner* — Adam Marcetich
(74) *Attorney, Agent, or Firm* — ASLAN LAW, P.C.

(57)          ABSTRACT

Equipment for the support of biomedical devices comprises a supporting frame; a first supporting device/apparatus/unit/component/structure or the like of a first biomedical device associated with the supporting frame; a second supporting device/apparatus/unit/component/structure or the like of a second biomedical device, of the type of a magnetic drive centrifugal pump provided with at least one rotor element and with motor device/apparatus/unit/component/structure or the like for the rotational actuation of the rotor element, associated with the supporting frame, one or more electrical connectors that can be connected to the electrical user points; at least one control and command unit operatively connected to the connectors and configured to process the data coming from the connectors; and a rechargeable power supply device/apparatus/unit/component/structure or the like associated with the supporting frame and electrically connected at least to the control and command unit.

2 Claims, 3 Drawing Sheets

(51) Int. Cl.
  *A61M 60/232*  (2021.01)
  *A61M 60/38*  (2021.01)

(52) U.S. Cl.
  CPC .......... *A61M 60/232* (2021.01); *A61M 60/38*
    (2021.01); *A61M 2205/8237* (2013.01); *A61M*
    *2209/086* (2013.01)

(58) Field of Classification Search
  CPC .......... A61M 1/3621; A61M 2209/082; A61M
    60/38; A61M 1/1621; A61M 2209/086;
    A61B 50/13; A61B 50/20; A61B 90/50
  See application file for complete search history.

(56) References Cited

U.S. PATENT DOCUMENTS

| | | | | |
|---|---|---|---|---|
| 5,516,226 | A * | 5/1996 | Wu | A61G 5/10 |
| | | | | 403/205 |
| 5,819,596 | A * | 10/1998 | De Filippo | B62D 1/04 |
| | | | | 74/552 |
| 5,894,273 | A * | 4/1999 | Meador | A61M 60/31 |
| | | | | 340/611 |
| 6,893,590 | B1 * | 5/2005 | Rigosi | C08J 5/128 |
| | | | | 264/275 |
| 8,576,143 | B1 * | 11/2013 | Kelly | G02B 27/017 |
| | | | | 359/630 |
| D850,625 | S * | 6/2019 | Schmid | D24/186 |
| 10,569,002 | B2 | 2/2020 | Bellini | |
| 2003/0076015 | A1 * | 4/2003 | Ehrenreich | A61B 50/13 |
| | | | | 312/209 |
| 2005/0004480 | A1 * | 1/2005 | Kirchhof | A61M 1/3666 |
| | | | | 604/4.01 |
| 2005/0027231 | A1 * | 2/2005 | Kirchhof | A61M 1/3623 |
| | | | | 604/4.01 |
| 2005/0063860 | A1 * | 3/2005 | Carpenter | A61M 60/113 |
| | | | | 604/4.01 |
| 2006/0222533 | A1 * | 10/2006 | Reeves | A61M 1/3666 |
| | | | | 417/423.1 |
| 2007/0293804 | A1 * | 12/2007 | Ghelli | A61M 1/3664 |
| | | | | 604/6.15 |
| 2009/0175762 | A1 * | 7/2009 | Ogihara | A61M 1/1698 |
| | | | | 422/46 |
| 2010/0140149 | A1 * | 6/2010 | Fulkerson | B01D 61/28 |
| | | | | 210/321.71 |
| 2011/0139738 | A1 * | 6/2011 | Raybuck | A61B 50/13 |
| | | | | 211/85.13 |
| 2011/0208108 | A1 * | 8/2011 | Muller-Spanka | A61M 1/3666 |
| | | | | 604/6.11 |
| 2013/0226064 | A1 * | 8/2013 | Galavotti | A61M 1/3623 |
| | | | | 604/4.01 |
| 2015/0323328 | A1 * | 11/2015 | Doyle | A61M 1/1621 |
| | | | | 701/23 |
| 2019/0038825 | A1 * | 2/2019 | Muller-Spanka | A61M 39/281 |
| 2019/0290380 | A1 * | 9/2019 | Jawidzik | A61B 50/10 |
| 2020/0129691 | A1 * | 4/2020 | Lacy | A61M 5/172 |
| 2020/0206400 | A1 * | 7/2020 | Shinohara | A61M 60/871 |
| 2020/0316283 | A1 * | 10/2020 | Vecten | A61M 1/365 |
| 2021/0205553 | A1 * | 7/2021 | Salmon | A61M 16/0875 |
| 2022/0023650 | A1 * | 1/2022 | Perl | A61M 16/1005 |

FOREIGN PATENT DOCUMENTS

| | | | | |
|---|---|---|---|---|
| CN | 114306791 A * | 4/2022 | | |
| DE | 102017104754 A1 * | 9/2018 | ....... | A61M 16/1005 |
| WO | WO 92/04060 A1 | 3/1992 | | |
| WO | WO-2012058778 A2 * | 5/2012 | ............ | F16M 13/02 |
| WO | WO 2020/152589 A1 | 7/2020 | | |

* cited by examiner

EQUIPMENT FOR THE SUPPORT OF BIOMEDICAL DEVICES DURING EXTRACORPOREAL CIRCULATION AND RELATED SYSTEM

CROSS-REFERENCE TO RELATED APPLICATIONS

This application claims priority to IT patent application No. 102021000014273 filed on May 27, 2021, and this application claims priority to and is a 371 of international PCT Application No. PCT/IB2022/055015 filed on May 27, 2022, the entire contents of which are hereby incorporated by reference.

TECHNICAL FIELD

The present invention relates to a piece of equipment for the support of biomedical devices during extracorporeal circulation, particularly for the support of an oxygenator and the related pumping unit.

BACKGROUND ART

As is well known, for certain surgical operations, during which the patient's heart functions are temporarily suspended, extracorporeal blood circuits are made using the so-called "heart-lung" machines.

Heart-lung machines provide for a number of devices, including a filtration device (also called "venous reservoir") adapted to filter the incoming blood from the patient, a heat exchanger adapted to regulate the temperature of the blood exiting the filtration device, and an oxygenator adapted to provide the proper oxygen supply to the blood intended to be fed back into the patient. Specifically, the incoming blood from the patient is sent to the oxygenator by means of a related pumping unit, which generally comprises a centrifugal pump of the dragging or magnetic levitation type, i.e., provided with a rotor element adapted to send the incoming blood towards the oxygenator due to the rotation thereof and with a stator element adapted to control the rotor element in rotation.

A set of parameters need to be monitored and controlled during extracorporeal circulation, including the number of revolutions of the rotor element and the flow rate of blood sent to the oxygenator.

Appropriately, equipment is used during extracorporeal circulation that supports the oxygenator and the pumping unit and provided with a processing unit to control and command the aforementioned parameters.

This equipment is generally used in both hospital and out-of-hospital settings, since the extracorporeal circulation is also applied under emergency situations, such as in roadside rescue, during which there is a need to adequately support the various devices in a dynamic context and in a flexible manner.

However, the equipment of known type for the support of biomedical devices, particularly for the support of the oxygenator and of the related pumping unit, has some drawbacks.

In particular, they do not allow for easy and practical support and movement of the oxygenator and the related pumping unit in out-of-hospital emergency situations wherein the patient is in places that are difficult to reach by emergency vehicles where there is a need to adequately support the various devices in a dynamic context and in a flexible manner.

In fact, these known types of equipment require an external power source such as the mains power or an uninterruptible power supply and, therefore, are not suitable for use in situations where health care workers need to reach the patient on foot while carrying the equipment needed for effective medical intervention.

In addition, these known types of equipment are bulky and, as a result, difficult for health care workers to carry by hand.

DESCRIPTION OF THE INVENTION

The main aim of the present invention is to devise a piece of equipment that enables practical and functional support of the oxygenator and the related pumping unit during the application of extracorporeal circulation to a patient both in hospital settings and in out-of-hospital emergency situations.

Within this aim, one object of the present invention is to devise a piece of equipment that is also easily transported manually by health care workers, thus enabling its use in emergency situations in which the patient is difficult to reach by the emergency vehicles.

Yet another object is to devise a piece of equipment which allows safe and easy connection with the sensors applied to the biomedical devices for monitoring the process parameters or with external auxiliary equipment.

Another object of the present invention is to devise a piece of equipment for the support of biomedical devices which allows the aforementioned drawbacks of the prior art to be overcome within a simple, rational, easy-to-use and cost-effective solution.

The aforementioned objects are achieved by this equipment for the support of biomedical devices according to the independent claim(s).

BRIEF DESCRIPTION OF THE DRAWINGS

Other characteristics and advantages of the present invention will become more apparent from the description of a preferred, but not exclusive, embodiment of a piece of equipment for the support of biomedical devices, illustrated by way of an indicative, yet non-limiting example, in the accompanying tables of drawings wherein.

EMBODIMENTS OF THE INVENTION

Figure 1:
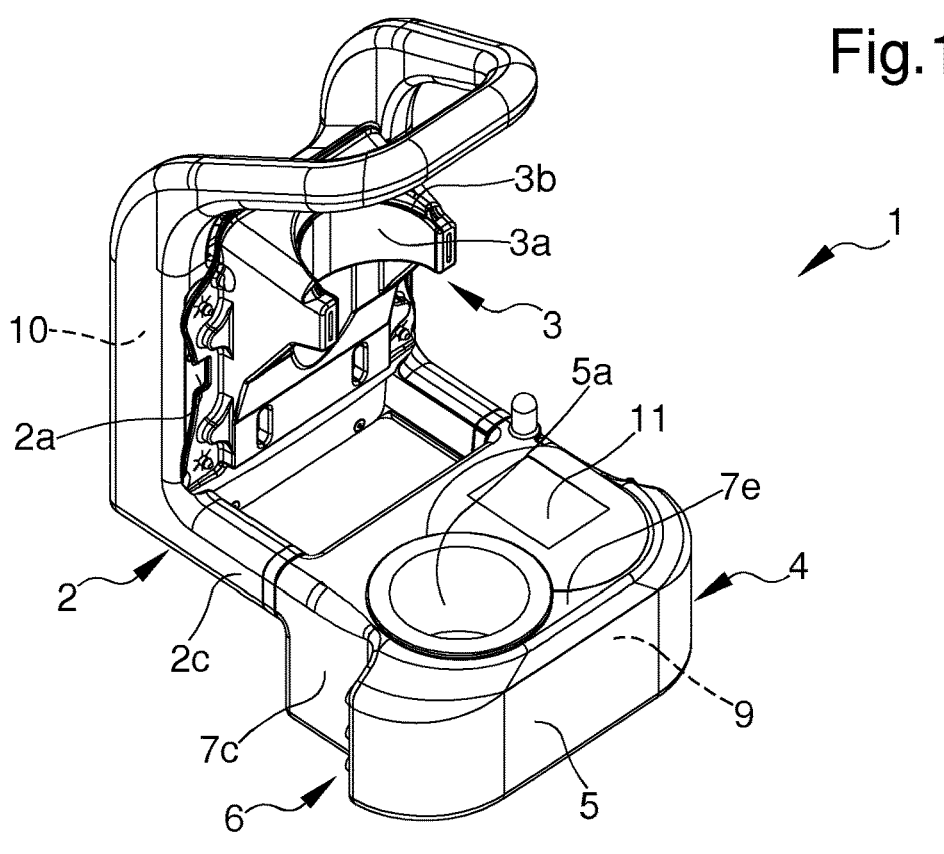
FIG. 1 is an axonometric view of a piece of equipment for the support of biomedical devices according to the invention.
Figure 2:
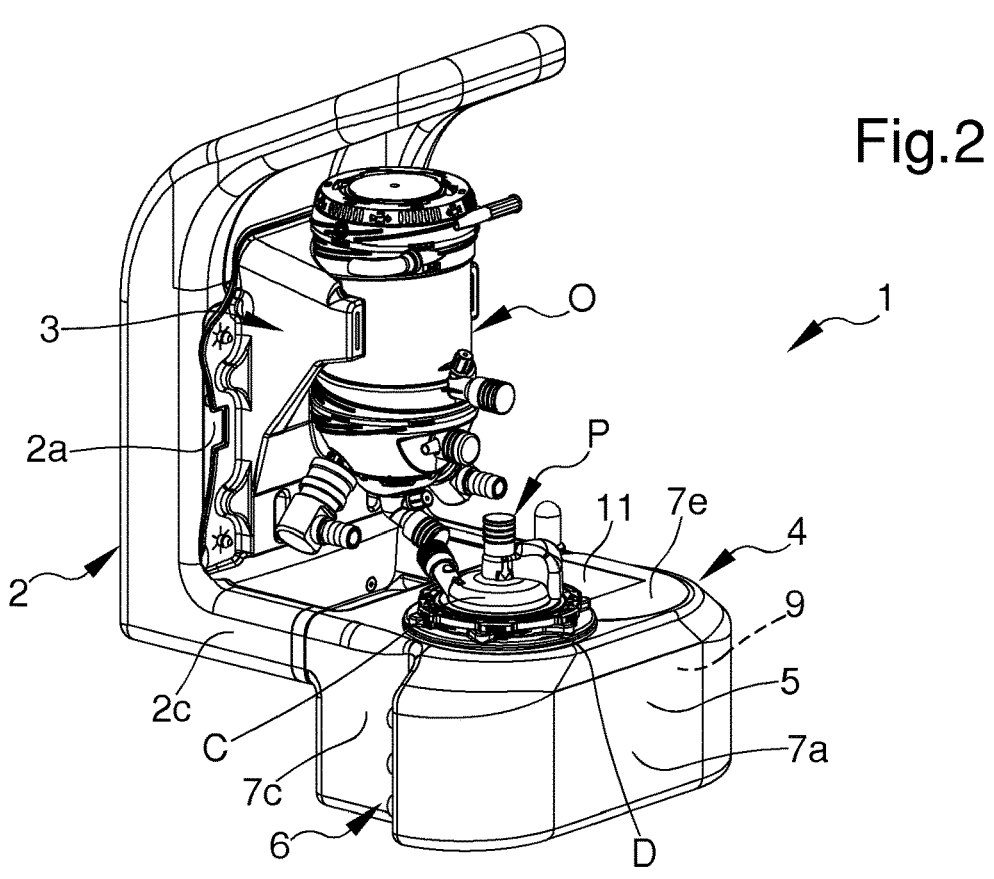
FIG. 2 is a first axonometric view of the equipment in FIG. 1 supporting the biomedical devices.
Figures 3, 5:
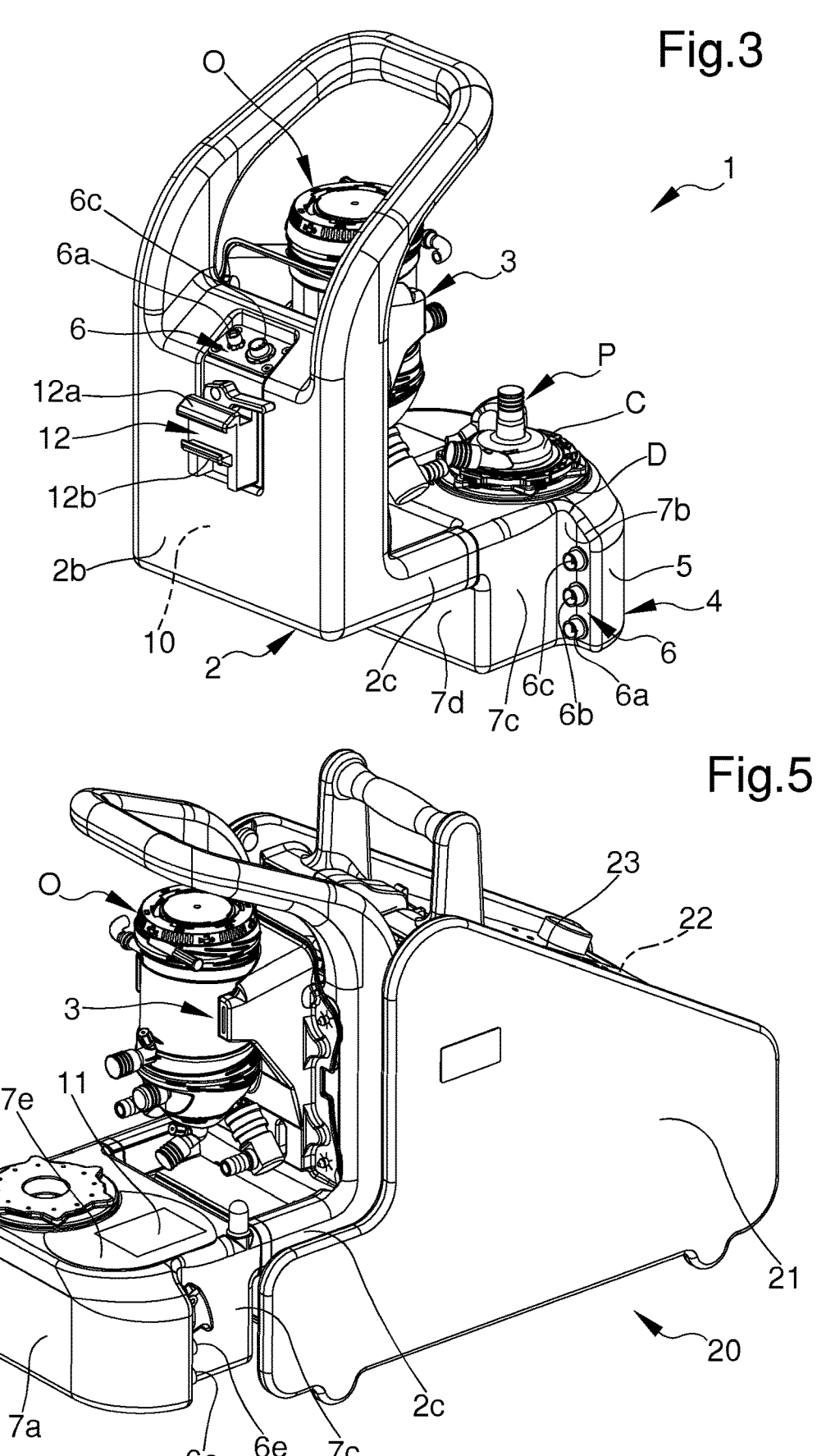
FIG. 3 is a second axonometric view of the equipment in FIG. 2.
FIG. 5 is an axonometric view of a system for the support of biomedical devices comprising the equipment in FIG. 2.

With particular reference to these figures, reference numeral 1 globally indicates a piece of equipment for the support of biomedical devices.

The equipment 1 comprises a supporting frame 2, first supporting means 3 of a first biomedical device O and second supporting means 4 of a second biomedical device P, where the first supporting means 3 and the second supporting means 4 are associated with the supporting frame 2.

More particularly, the first biomedical device O is of the type of an oxygenator adapted to provide the proper supply of oxygen to the blood intended to be fed back into the patient and to remove carbon dioxide from the blood itself.

Appropriately, the first supporting means 3 comprise a first seat 3a intended to receive the oxygenator O. In more detail, the first seat 3a is shaped so as to receive the oxygenator O by interlocking and has at least one abutment surface 3b adapted to support the oxygenator itself.

Preferably, the first supporting means 3 are associated with the supporting frame 2 in a removable manner.

According to the invention, the second biomedical device P is of the type of a magnetic drive centrifugal pump provided with at least one rotor element and with motor means for the rotational actuation of the rotor element (the rotor element and the motor means are not visible in detail in the figures). Advantageously, the second supporting means 4 comprise at least one containment body 5 associated with the supporting frame 2 and adapted to support the centrifugal pump P.

The rotor element is contained within a hollow body identified in the figures by the letter C. More particularly, the motor means comprise a containment body D inside which is inserted a stator element adapted to generate a magnetic field to command in rotation the rotor element around a relevant axis X, without contact. The methods of controlling the rotation of the rotor element, although not covered by the present invention, are widely known to the engineer in the field.

Specifically, the stator element comprises a plurality of windings intended to be crossed by the electric current for the formation of one or more magnetic fields adapted to interact with the rotor element to lift it and bring it into rotation around the relevant axis X.

In more detail, the containment body 5 defines a second housing seat 5a intended to receive the motor means of the centrifugal pump P. The motor means of the centrifugal pump P are then housed inside the second seat 5a and the rotor element is connectable to the motor means in a removable manner. Specifically, the containment body D is inserted within the second seat 5a and the hollow body C is associated with the containment body D in a removable manner. The motor means can be locked together with the containment body 5.

At least one of either the supporting frame 2 or the containment body 5 comprises one or more electrical connectors 6 which can be connected to the electrical user points.

Preferably, both the supporting frame 2 and the containment body 5 comprise one or more electrical connectors 6.

Advantageously, the connectors 6 are selected from the group comprising: at least a first connector 6a connectable to an external power supply source, at least a second connector 6b connectable to a flow sensor, at least a third connector 6c connectable to a pressure sensor, at least a fourth connector 6d of the type of a USB port, at least a fifth connector 6e connectable to an external processing unit. Preferably, the equipment 1 comprises at least one connector 6a,6b,6c,6d,6e of each of the types listed above.

In the preferred embodiment shown in the figures, the containment body 5 comprises at least one outer face 7a facing, in use, outwardly, and at least one inner face 7b, opposite the outer face and facing the side of the supporting frame 2. A plurality of connectors 6 are arranged on the inner face 7b.

More particularly, the connectors 6 arranged on the inner face 7b are substantially vertically aligned with each other.

Appropriately, the containment body 5 comprises at least one side face 7c arranged adjacent and transverse to the inner face 7b, wherein the side face 7c extends away from the outer face 7a, i.e., towards the supporting frame 2, to define a recess.

This special shape of the containment body 5 allows the connectors 6 arranged on the inner face 7b to be protected from accidental blows and minimizes the side overall dimensions.

Preferably, the containment body 5 comprises two inner faces 7b arranged on opposite sides to each other with respect to a median plane.

As visible from the figures, the inner faces 7b are coplanar with each other.

In the embodiment shown in the figures, the containment body 5 comprises at least one mating face 7d associated with the supporting frame 2 and which is staggered from the inner faces 7b. The inner faces 7b are positioned between mating face 7d and the outer face 7a.

More particularly, the containment body 5 also has an upper face 7e, facing upwards in use, on which the second seat 5a is formed.

According to the invention, the equipment 1 also comprises at least one control and command unit 9, operatively connected to said connectors 6 and configured to process the data from the connectors themselves, and rechargeable power supply means 10 associated with the supporting frame 2 and electrically connected to the control and command unit 9. In particular, the power supply means 10 are also electrically connected to the motor means housed within the second seat 5a. The control and command unit 9 is provided with a microprocessor.

Advantageously, the control and command unit 9 is arranged internally to the containment body 5.

Appropriately, at least one display 11 adapted to graphically display the quantities processed by the control and command unit 9 is also arranged on the upper face 7e.

Preferably, the supporting frame 2 is internally hollow and the power supply means 10, of the type of a rechargeable battery, are arranged internally to the supporting frame itself.

More particularly, the power supply means 10 are arranged at the first supporting means 3.

The equipment 1 also comprises electrical interconnection means, of the type of one or more electrical connection cables not shown in detail in the figures, for electrically interconnecting the power supply means 10 at least to the control and command unit 9, where such interconnection means are at least partly housed inside the supporting frame itself. The interconnecting means may also be adapted to connect the power supply means 10 to the motor means of the centrifugal pump P.

In more detail, the supporting frame 2 comprises at least one supporting surface 2a, with which the first supporting means 3 are associated, and one anchoring surface 2b opposite the supporting surface 2a. The power supply means 10 are positioned between the supporting surface 2a and the anchoring surface 2b.

Figure 4:
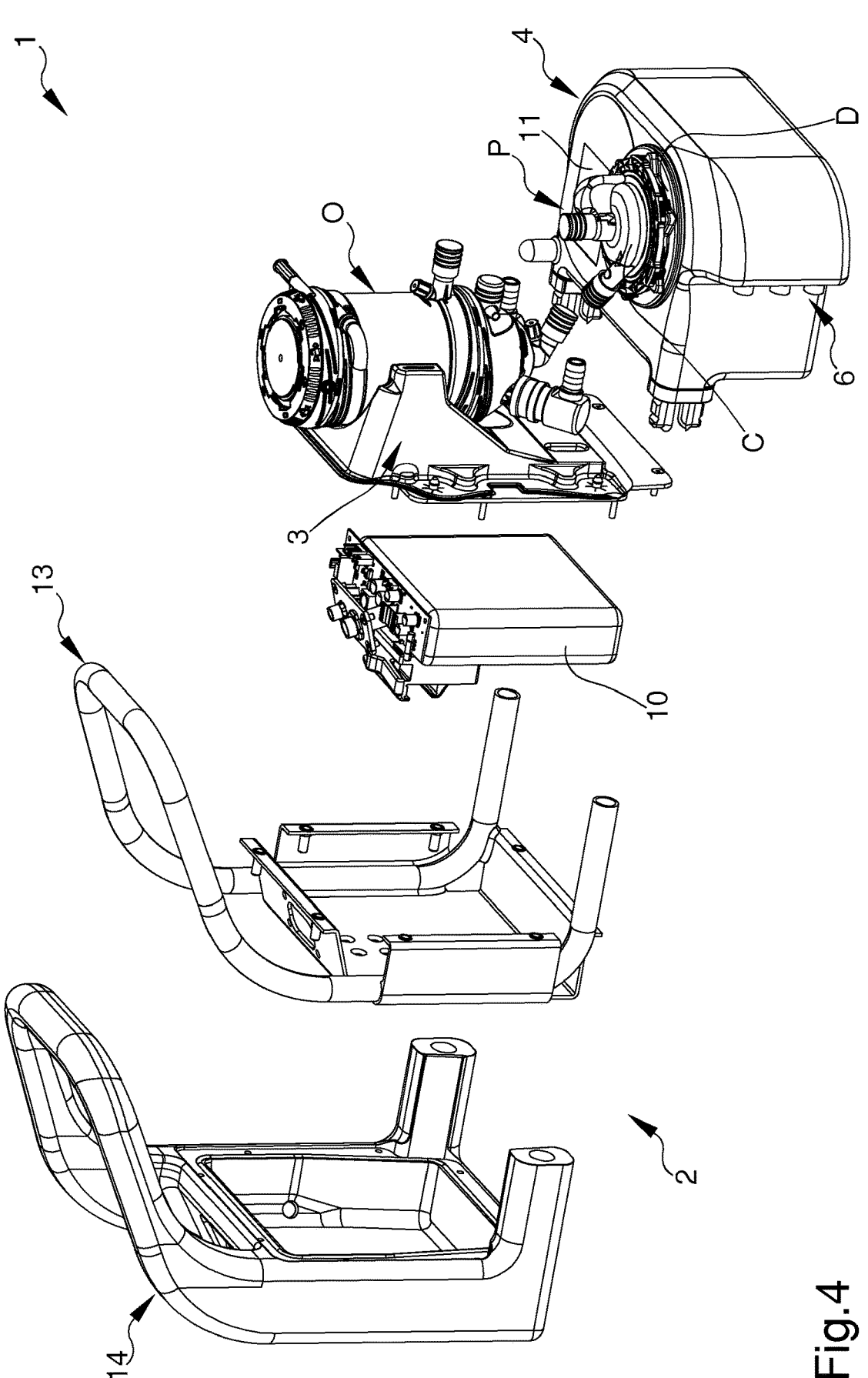
FIG. 4 is a partly exploded view of the equipment in FIG. 2.

In the preferred embodiment shown in FIG. 4, the supporting frame 2 comprises a tubular structure 13 and an enclosure 14 covering the tubular structure 13. In more detail, the tubular structure 13 is made of a metal material and the enclosure 14 is made of an elastomeric material, e.g., integral polyurethane, which is applied to the tubular structure 13 by over-molding. In this embodiment, the power supply means 10 are associated with the tubular structure 13 and contained inside the enclosure 14.

In an alternative embodiment, the supporting frame 2 is made of a composite material, such as e.g. of the type of resin-impregnated carbon fiber.

Appropriately, at least some of the electrical connectors 6 are defined on the anchoring surface 2b.

Advantageously, the equipment 1 also comprises wireless transmission means operatively connected to the control and command unit 9 and adapted to transfer the data processed by the latter to a remote display unit, of the type of a smart-phone, tablet or computer.

In the embodiment shown in the figures, the supporting frame 2 comprises connection means 2c to the containment body 5.

More particularly, the connection means 2c comprise at least one pair of tubular elements directly associated with the mating face 7d of the containment body 5. The interconnection means adapted to electrically connect the power supply means 10 to the motor means and to the control and command unit 9 are housed inside at least one of the tubular elements 2c.

Advantageously, the supporting frame 2 is provided with anchoring means 12 which can be associated with a load-bearing body 21. More particularly, the anchoring means 12 comprise a fixed element 12a and a movable element 12b that can be moved close to/away from the fixed element 12a to engage/release the load-bearing body 21.

More particularly, the anchoring means 12 are associated with the anchoring surface 2b of the supporting frame 2.

The present invention also refers to a system 20 for the support of biomedical devices, shown in FIG. 4, comprising a load-bearing body 21, at least one additional connector connectable to at least one sensor adapted to measure venous oxygen saturation and at least one processing unit 22 associated with the load-bearing body 21 and operatively connected to the additional connector and to a display 23. The processing unit 22 is configured to process the data coming from the additional connector and to display them in a graphical form on the display 23.

According to the invention, the system 20 also comprises the piece of equipment 1 where the supporting frame 2 is associated with the load-bearing body 21 and comprises electrical connecting means, not shown in the figures, of the fifth connector 6e to the processing unit 22, so as to operatively connect the control and command unit 9 to the processing unit 22. The processing unit 22 is configured to display the data processed by the control and command unit 9 in a graphical form on the display 23.

In more detail, the supporting frame 2 is associated with the load-bearing body 21 through the anchoring means 12.

Advantageously, the equipment 1 comprises an electrical power supply unit associated with the load-bearing body 21, which is operatively connected to the motor means and to the control and command unit 9 by means of the aforementioned electrical connection means.

The operation of this invention is as follows.

The oxygenator O and the centrifugal pump P are initially installed on the piece of equipment 1. More particularly, the oxygenator O is associated with the first supporting means 3, e.g., inserting it by interlocking inside the first seat 3a, and the centrifugal pump P is associated with the second supporting means 4, e.g., inserting the motor means inside the second seat 5a.

Next, a flow sensor is connected to the second connector 6b and a pressure sensor to the third connector 6c. The oxygenator O and the centrifugal pump P are also connected to each other as well as to the extracorporeal circulation circuit applied to the patient.

The equipment 1 is then found to be ready for operation.

Specifically, during extracorporeal circulation, the power supply means 10 supply both the control and command unit 9 and the motor means, thus enabling the autonomous operation of the equipment 1 and the proper course of extracorporeal circulation.

During operation, the control and command unit 9 receives and processes the signals received from the sensors through the connectors 6 and provides a graphical representation thereof on the display 11.

If the power supply means 10 become discharged during use, an external power source can be connected to the first connector 6a so as to ensure the operation of the power supply means and of the control and command unit 9.

Once the patient is brought to a rescue vehicle or hospital environment, the equipment 1 can be connected to an external power source, via the first connector 6a, or it can be placed inside the system 20 by associating its supporting frame 2 with the load-bearing body 21 and by connecting the processing unit 22 to the control and command unit 9 via the fifth connector 6e. In this way, the data processed by the control and command unit 9 are transferred to the processing unit 22, which provides a graphical representation thereof on the display 23 attached to the load-bearing body 21.

As a result of the connection between the processing unit 22 and the control and command unit 9, the power supply unit that powers the processing unit 22 also powers the motor means and the control and command unit 9 of the equipment 1.

In actual facts, it has been ascertained that the described invention achieves the intended objects, and in particular, the fact is emphasized that the equipment covered by this invention enables the practical and effective implementation of the extracorporeal circulation even under emergency conditions, wherein no fixed power supply line is available and wherein health care workers must independently reach the patient to be rescued.

In practice, due to the presence of the rechargeable power supply means associated with the supporting frame, the equipment according to the invention is capable of autonomously operating an extracorporeal blood circulation circuit, while at the same time, it can be easily carried by hand by a health care worker.

Again, the positioning of the electrical connectors on the containment body allows for easy connection to external user points while minimizing the overall dimensions, so as to obtain a compact solution, thus reducing the risk that the cables connected to the connectors themselves could be accidentally bumped while using the equipment.

In addition, the equipment covered by the present invention is capable of integrating into a system for the support of biomedical devices provided with an autonomous processing unit, so that it can then also be used in a hospital environment.

The invention claimed is:

1. A system for the support of biomedical devices during extracorporeal circulation, the system comprising:
   a load-bearing body;
   a connector connectable to a venous saturation sensor;
   a processing unit associated with said load-bearing body and operatively connected to said connector and a display, said processing unit being configured to process data received from said connector and to graphically display said data on said display;
   a piece of equipment for the support of biomedical devices,
   the equipment comprising:

a supporting frame;

first supporting means of a first biomedical device associated with said supporting frame;

second supporting means of a second biomedical device, a magnetic drive centrifugal pump provided with a rotor element, wherein the second supporting means comprise a motor means for a rotational actuation of the rotor element, wherein the motor means is associated with said supporting frame;

one or more electrical connectors connectable to the electrical user points;

a control and command unit operatively connected to said one or more electrical connectors and configured to process data coming from said one or more electrical connectors;

rechargeable power supply means associated with said supporting frame and electrically connected to said at least one control and command unit, wherein said supporting frame is associated with said load-bearing body; and electrical connecting means of said connector to said processing unit to operatively connect said control and command unit to said processing unit, and configured to graphically display on said display the data processed by said control and command unit.

2. An equipment for the support of biomedical devices, the equipment comprising:

a supporting frame;

first supporting means of a first biomedical device associated with said supporting frame;

second supporting means of a second biomedical device;

one or more electrical connectors connectable to electrical user points;

a control and command unit operatively connected to said one or more electrical connectors and configured to process data coming from said one or more electrical connectors;

rechargeable power supply means associated with said supporting frame and electrically connected to said control and command unit;

wherein the supporting frame is internally hollow and the power supply means are arranged internally to the supporting frame, wherein said supporting frame comprises a supporting surface, with which said first supporting means is/are associated, and an anchoring surface opposite said supporting surface, and said rechargeable power supply means is/are positioned between said supporting surface and said anchoring surface, wherein the supporting frame comprises a tubular structure and an enclosure covering the tubular structure, the tubular structure being made of a metal material and the enclosure being made of an elastomeric material, which is applied to the tubular structure by over-molding, the power supply means being associated with the tubular structure and contained inside the enclosure.

* * * * *